United States Patent [19]
Theisen

[11] Patent Number: 5,972,374
[45] Date of Patent: Oct. 26, 1999

[54] CHEWING GUM WITH TEETH WHITENER

[76] Inventor: Thomas Theisen, 1720 Venture Farms Rd., Pilot Point, Tex. 76258

[21] Appl. No.: 09/054,241

[22] Filed: Apr. 2, 1998

[51] Int. Cl.[6] .............................. A61K 7/16; A61K 7/20; A61K 9/68; A61K 9/44
[52] U.S. Cl. ............................ 424/440; 424/48; 424/49; 424/53; 424/401; 424/435; 424/467; 424/613; 424/616; 426/3; 426/5; 426/282; 426/514; 426/532; 426/539; 426/548; 426/561
[58] Field of Search .......................... 426/35, 539, 282, 426/514, 532, 548, 561; 424/467, 53, 440, 401, 435, 48, 49, 613, 616

[56] References Cited

U.S. PATENT DOCUMENTS

| | | | |
|---|---|---|---|
| D. 271,439 | 11/1983 | Schumacher | D1/12 |
| 810,210 | 1/1906 | Laws | 426/3 |
| 1,072,338 | 9/1913 | Lehman | 426/3 |
| 1,429,405 | 9/1922 | Carter et al. | |
| 1,566,329 | 12/1925 | Laskey | |
| 2,015,097 | 9/1935 | Bowman et al. | 107/19 |
| 2,874,649 | 2/1959 | Pelletier | 107/54 |
| 3,806,290 | 4/1974 | Graff et al. | 425/133 |
| 3,857,963 | 12/1974 | Graff et al. | 426/3 |
| 3,894,154 | 7/1975 | Graff et al. | 426/5 |
| 4,156,740 | 5/1979 | Glass et al. | 426/3 |
| 4,302,441 | 11/1981 | Muhleman et al. | 424/48 |
| 4,786,243 | 11/1988 | Kehoe | 425/131.1 |
| 4,835,000 | 5/1989 | Kehoe | 426/516 |
| 4,847,090 | 7/1989 | Della Posta et al. | 424/440 |
| 4,847,900 | 7/1989 | Della Posta et al. | 424/440 |
| 4,975,288 | 12/1990 | Hager et al. | 426/5 |
| 5,110,583 | 5/1992 | Sampathkumar | 424/48 |
| 5,125,819 | 6/1992 | Hager et al. | 425/133.1 |
| 5,500,207 | 3/1996 | Goulet | 424/54 |
| 5,626,892 | 5/1997 | Kehoe et al. | 426/3 |
| 5,631,000 | 5/1997 | Pellico et al. | 424/53 |
| 5,693,334 | 12/1997 | Miskewitz | 424/440 |
| 5,718,886 | 2/1998 | Pellico | 424/53 |
| 5,785,957 | 7/1998 | Losee et al. | 424/53 |

FOREIGN PATENT DOCUMENTS

| | | |
|---|---|---|
| 93 00884 | 1/1993 | WIPO . |
| 97 07777 | 3/1997 | WIPO . |
| 97 12589 | 4/1997 | WIPO . |
| 97 21417 | 6/1997 | WIPO . |
| 98 10737 | 3/1998 | WIPO . |
| 98 10738 | 3/1998 | WIPO . |
| 98 40047 | 9/1998 | WIPO . |

*Primary Examiner*—Shep K. Rose

[57] ABSTRACT

A new chewing gum with teeth whitener for helping whiten and brighten teeth while helping freshen the breath. The inventive device includes an elongate gum member having a central bore extending along its longitudinal axis. Extending through the central bore to substantially fill the central bore is a whitening gel which includes a whitening agent for whitening teeth while chewing the gum. The elongate gum member is divided along its length into a plurality of separable chewing portions such that each chewing portion includes portion of the gum member and a portion of the whitening gel member.

9 Claims, 2 Drawing Sheets

5,972,374

CHEWING GUM WITH TEETH WHITENER

BACKGROUND OF THE INVENTION

1. Field of the Invention

The present invention relates to chewing gum and more particularly pertains to a new chewing gum with teeth whitener for helping whiten and brighten teeth while helping freshen the breath.

2. Description of the Prior Art

The use of chewing gum is known in the prior art. More specifically, chewing gum heretofore devised and utilized are known to consist basically of familiar, expected and obvious structural configurations, notwithstanding the myriad of designs encompassed by the crowded prior art which have been developed for the fulfillment of countless objectives and requirements.

Known prior art chewing gum include U.S. Pat. No. 5,405,623; U.S. Pat. No. 5,192,562; U.S. Pat. No. 5,085,872; U.S. Pat. No. 5,145,696; U.S. Pat. No. 4,986,991; and U.S. Pat. No. Des. 271,439.

While these devices fulfill their respective, particular objectives and requirements, the aforementioned patents do not disclose a new chewing gum with teeth whitener. The inventive device includes an elongate gum member having a central bore extending along its longitudinal axis. Extending through the central bore to substantially fill the central bore is a whitening gel which includes a whitening agent for whitening teeth while chewing the gum. The elongate gum member is divided along its length into a plurality of separable chewing portions such that each chewing portion includes portion of the gum member and a portion of the whitening gel member.

In these respects, the chewing gum with teeth whitener according to the present invention substantially departs from the conventional concepts and designs of the prior art, and in so doing provides an apparatus primarily developed for the purpose of helping whiten and brighten teeth while helping freshen the breath.

SUMMARY OF THE INVENTION

In view of the foregoing disadvantages inherent in the known types of chewing gum now present in the prior art, the present invention provides a new chewing gum with teeth whitener construction wherein the same can be utilized for helping whiten and brighten teeth while helping freshen the breath.

The general purpose of the present invention, which will be described subsequently in greater detail, is to provide a new chewing gum with teeth whitener apparatus and method which has many of the advantages of the chewing gum mentioned heretofore and many novel features that result in a new chewing gum with teeth whitener which is not anticipated, rendered obvious, suggested, or even implied by any of the prior art chewing gum, either alone or in any combination thereof.

To attain this, the present invention generally comprises an elongate gum member having a central bore extending along its longitudinal axis. Extending through the central bore to substantially fill the central bore is a whitening gel which includes a whitening agent for whitening teeth while chewing the gum. The elongate gum member is divided along its length into a plurality of separable chewing portions such that each chewing portion includes portion of the gum member and a portion of the whitening gel member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new chewing gum with teeth whitener apparatus and method which has many of the advantages of the chewing gum mentioned heretofore and many novel features that result in a new chewing gum with teeth whitener which is not anticipated, rendered obvious, suggested, or even implied by any of the prior art chewing gum, either alone or in any combination thereof.

It is another object of the present invention to provide a new chewing gum with teeth whitener which may be easily and efficiently manufactured and marketed.

It is a further object of the present invention to provide a new chewing gum with teeth whitener which is of a durable and reliable construction.

An even further object of the present invention is to provide a new chewing gum with teeth whitener which is susceptible of a low cost of manufacture with regard to both materials and labor, and which accordingly is then susceptible of low prices of sale to the consuming public, thereby making such chewing gum with teeth whitener economically available to the buying public.

Still yet another object of the present invention is to provide a new chewing gum with teeth whitener which provides in the apparatuses and methods of the prior art some of the advantages thereof, while simultaneously overcoming some of the disadvantages normally associated therewith.

Still another object of the present invention is to provide a new chewing gum with teeth whitener for helping whiten and brighten teeth while helping freshen the breath.

Yet another object of the present invention is to provide a new chewing gum with teeth whitener which includes an elongate gum member having a central bore extending along its longitudinal axis. Extending through the central bore to substantially fill the central bore is a whitening gel which includes a whitening agent for whitening teeth while chewing the gum. The elongate gum member is divided along its length into a plurality of separable chewing portions such that each chewing portion includes portion of the gum member and a portion of the whitening gel member.

Still yet another object of the present invention is to provide a new chewing gum with teeth whitener that conveniently whitens teeth while chewing.

Even still another object of the present invention is to provide a new chewing gum with teeth whitener that allows you to freely move about while whitening your teeth rather than having to use a typical bleaching mouthpiece for holing a teeth whitening agent.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
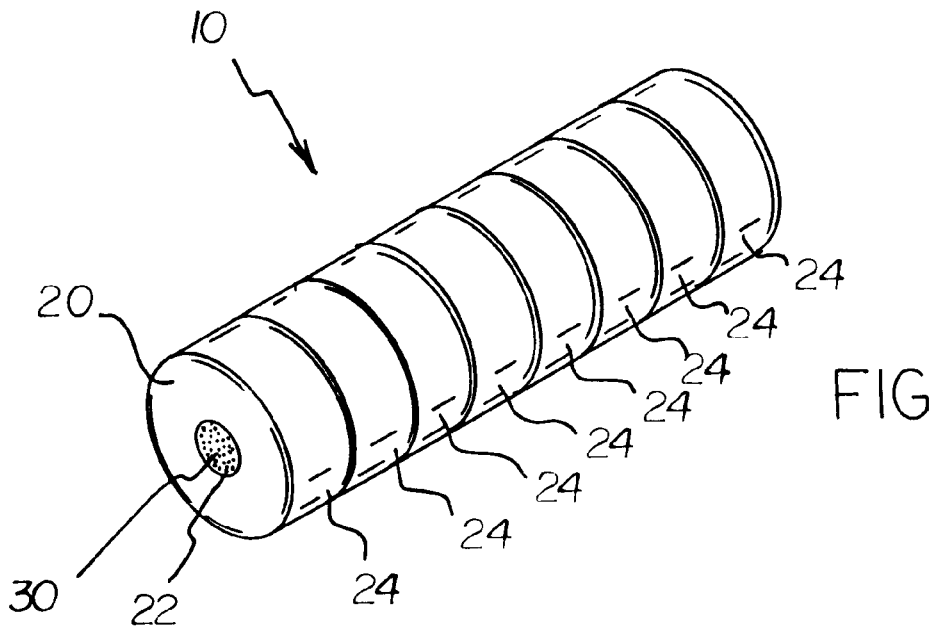
FIG. 1 is a schematic perspective view of a new chewing gum with teeth whitener according to the present invention.
Figure 2:
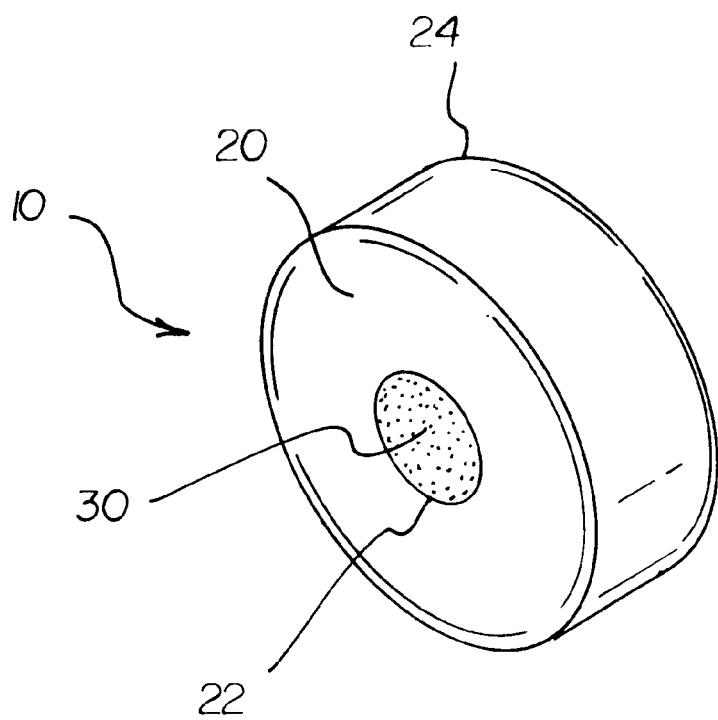
FIG. 2 is a schematic perspective view of a chewing portion of the present invention.
Figure 3:
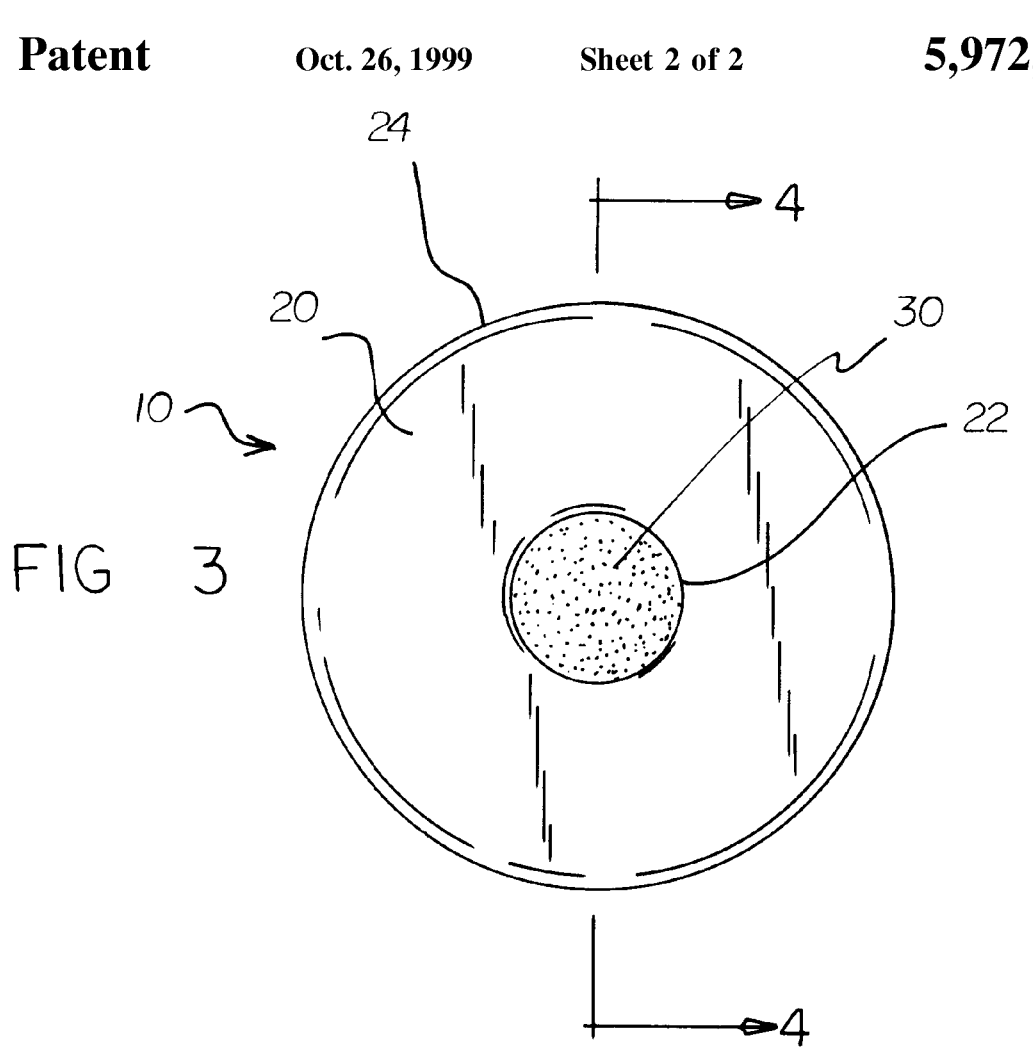
FIG. 3 is a schematic side view of a chewing portion of the present invention.
Figure 4:
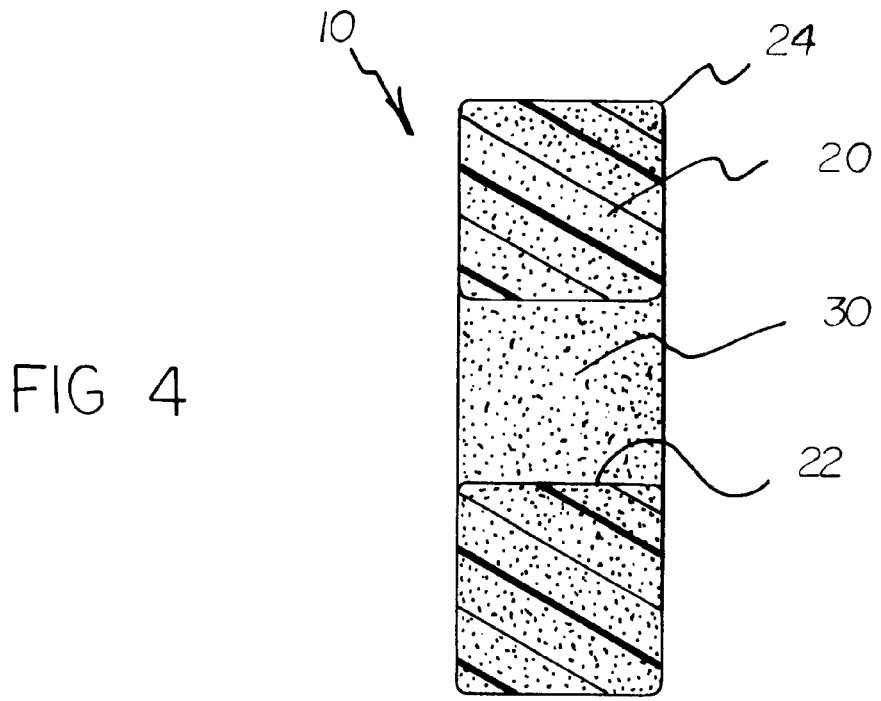
FIG. 4 is a schematic cross-sectional view of a chewing portion of the present invention taken from line 4—4 of FIG. 3.

With reference now to the drawings, and in particular to FIGS. 1 through 4 thereof, a new chewing gum with teeth whitener embodying the principles and concepts of the present invention and generally designated by the reference numeral 10 will be described.

As best illustrated in FIGS. 1 through 4, the chewing gum with teeth whitener 10 generally comprises an elongate gum member 20 having a central bore 22 extending along its longitudinal axis. Extending through the central bore 22 to substantially fill the central bore 22 is a whitening gel 30 which includes a whitening agent for whitening teeth while chewing the gum 10. The elongate gum member 20 is divided along its length into a plurality of separable chewing portions 24 such that each chewing portion 24 includes portion of the gum member 20 and a portion of the whitening gel member 30.

As shown in FIG. 1, the gum member 20 is generally cylindrical in shaped so that when divided, it forms cylindrical or disk shaped chewing portions 24. Preferably, the gum member 20 is divided so that the chewing portions 24 are bite sized for convenient chewing.

The gum member 20 is preferably made from common sugarfree type chewing gum recipes. Ideally, the gum member 20 ingredients include sorbitol, gum base, mannitol, glycerin, acesulfame potassium, softeners, aspartame, and flavoring. Similarly, the whitening gel 30 is to include commonly known teeth whitening agents so that the agents whiten a users teeth while the user chews on the gum 10. Ideally, the whitening gel includes glycerin, urea peroxide, water, polysorbate 20, triethanalamine, carbomer, disodium EDTA, sodium benzoate, potassium sorbate, sodium citrate, and flavoring. Any common flavoring, such as mint flavoring and cinnamon flavoring, may be included in both the gum member 20 and the whitening gel 30 to provide a pleasant and tasty flavor to the chewing gum.

In use, a chewing portion 24 is chewed by a user for a period time to permit the whitening agents in the whitening gel 30 to whiten the user's teeth. The flavorings of the gum member 20 and the gel 30 also help to freshen the user's breath while chewing.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A teeth whitening chewing gum, comprising:
    an elongate cylindrical gum member having a longitudinal axis, and a central bore extending along said longitudinal axis;
    a whitening gel being extended through said central bore to substantially fill said central bore, said whitening gel including a whitening agent for whitening teeth;
    said elongate gum member being divided along its length into a plurality of separable chewing portions such that each chewing portion includes portion of said gum member and a portion of said whitening gel member;
    each of said chewing portions having rounded outer edges;
    each of said chewing portions having rounded inner edges;
    wherein an inner diameter of said central bore is less than about ⅓ of an outer diameter of said gum member; and
    wherein a width of each of said chewing portions parallel said longitudinal axis of said gum member is substantially equal to a distance between inner and outer radii of said chewing portion.

2. The teeth whitening chewing gum of claim 1, wherein said gum member is cylindrical, wherein said chewing portions are cylindrical.

3. The teeth whitening chewing gum of claim 1, wherein said gum member comprises sorbitol, gum base, mannitol, glycerin, acesulfame potassium, aspartame, and flavoring.

4. The teeth whitening chewing gum of claim 3, wherein said flavoring of said gum member comprises a cinnamon flavor.

5. The teeth whitening chewing gum of claim 3, wherein said flavoring of said gum member comprises a mint flavor.

6. The teeth whitening chewing gum of claim 1, wherein said whitening gel comprises glycerin, urea peroxide, water, polysorbate 20, triethanalamine, carbomer, disodium EDTA, sodium benzoate, potassium sorbate, sodium citrate, and flavoring.

7. The teeth whitening chewing gum of claim 6, wherein said flavoring of said whitening gel comprises a cinnamon flavor.

8. The teeth whitening chewing gum of claim 6, wherein said flavoring of said whitening gel comprises a mint flavor.

9. A teeth whitening chewing gum, comprising:

an elongate cylindrical gum member having a longitudinal axis, and a central bore extending along said longitudinal axis, said longitudinal axis of said gum member being straight, said gum member having a constant outer diameter along said longitudinal axis;

wherein said gum member comprises sorbitol, gum base, mannitol, glycerin, acesulfame potassium, aspartame, and flavoring;

a whitening gel being extended through said central bore to substantially fill said central bore, said whitening gel including a whitening agent for whitening teeth;

wherein said whitening gel comprises glycerin, urea peroxide, water, polysorbate 20, triethanalamine, carbomer, disodium EDTA, sodium benzoate, potassium sorbate, sodium citrate, and flavoring;

said elongate cylindrical gum member being divided along its length into eight separable cylindrical chewing portions such that each chewing portion includes a portion of said gum member and a portion of said whitening gel member;

each of said chewing portions having rounded outer edges;

each of said chewing portions having rounded inner edges;

wherein an inner diameter of said central bore is less than about $\frac{1}{3}$ of an outer diameter of said gum member; and wherein a width of each of said chewing portions parallel said longitudinal axis of said gum member is substantially equal to a distance between inner and outer radii of said chewing portion.

\* \* \* \* \*